United States Patent [19]

Edmondson et al.

[11] Patent Number: 5,008,202

[45] Date of Patent: Apr. 16, 1991

[54] BLOOD DILUENT FOR RED BLOOD CELL ANALYSIS

[75] Inventors: Sherburne M. Edmondson, Sunnyvale; Carlos E. Luna, Campbell, both of Calif.

[73] Assignee: Sequoia Turner Corporation, Mountain View, Calif.

[21] Appl. No.: 277,334

[22] Filed: Nov. 29, 1988

[51] Int. Cl.$^5$ .......................................... G01N 31/00
[52] U.S. Cl. .......................................... 436/18; 436/8
[58] Field of Search .......................................... 436/18

[56] References Cited

U.S. PATENT DOCUMENTS

| | | | |
|---|---|---|---|
| 2,836,537 | 5/1958 | Skaptason | 167/22 |
| 3,236,733 | 4/1965 | Karisten et al. | |
| 3,281,366 | 11/1965 | Judge et al. | |
| 3,412,037 | 1/1966 | Gochman et al. | |
| 3,632,735 | 3/1970 | Kita | |
| 3,874,852 | 7/1974 | Hamill | |
| 3,962,125 | 6/1976 | Armstrong | 436/17 |
| 4,099,917 | 7/1977 | Kim | |
| 4,102,810 | 3/1976 | Armstrong | |
| 4,116,635 | 3/1977 | Jaeger | |
| 4,136,161 | 3/1976 | Falkowski | |
| 4,185,964 | 2/1977 | Lancaster | |
| 4,206,077 | 8/1978 | Sarstedt et al. | |
| 4,213,876 | 8/1978 | Crews et al. | |
| 4,219,440 | 6/1979 | Runck et al. | |
| 4,244,837 | 12/1979 | Crews et al. | |
| 4,248,634 | 5/1979 | Forester | |
| 4,250,051 | 12/1978 | Armstrong | |
| 4,264,470 | 5/1979 | Chastain et al. | |
| 4,286,963 | 11/1979 | Ledis et al. | |
| 4,297,238 | 10/1981 | Vormbrock et al. | 436/17 |
| 4,299,726 | 5/1979 | Crews et al. | |
| 4,336,029 | 8/1980 | Natale | |
| 4,346,018 | 6/1980 | Carter | |
| 4,358,394 | 8/1981 | Crews et al. | |
| 4,389,490 | 5/1981 | Crews et al. | |
| 4,390,632 | 7/1980 | Carter | |
| 4,405,719 | 5/1981 | Crews et al. | |
| 4,485,175 | 11/1984 | Ledis et al. | |
| 4,493,821 | 2/1982 | Harrison | |
| 4,521,518 | 6/1985 | Carter | |
| 4,529,705 | 6/1983 | Larsen | |
| 4,617,275 | 10/1986 | Matsuda et al. | |
| 4,637,986 | 8/1983 | Brown et al. | |
| 4,745,071 | 10/1986 | Lapicola et al. | |
| 4,780,419 | 10/1988 | Uchida et al. | 436/8 |

OTHER PUBLICATIONS

Hatch, A. and Balazs, T., *Am. J. Clin. Path.*, 36: 220–223 (1961), "The Use of Cetavlon in a Diluent for Counting Leukocytes and the Coulter Electronic Counter".

Allen, J. D. and Gudaitis, A. V., *Am. J. Clin. Path.*, 33: 553–556 (1960), "Diluting Fluid for Electronic Counting of Leukocytes and Hemoglobin Determinations".

D'Angelo, G. and LaCombe, M., *Am. J. Clin. Path.*, 39: 658–662 91962), "A Practical Diluent for Electronic White Cell Counts".

Van Dilla, M. A., Fulwyler, M. J. and Boone, I. U., P.S.E.B.M. 125: 367–370 (1967), "Volume Distribution and Separation of Normal Human Leukocytes".

Wintrobe, M. M. (ed.) Clinical Hematology, (6th Edition) (Lea and Febiger, Philadelphia, 1974), Ch. 1, "The Approach to Hematologic Problems".

Sankyo Company Ltd., Chemical Extracts vol. 80, No. 23 (Jun. 10, 1974), Abstract 12965W, p. 134.

Scott et al., Chemical Abstracts vol. 81, No. 5 (Aug. 5, 1974), Abstract 21782U, p. 114.

Schuetz et al., Chemical Abstracts, vol. 97, No. 7 (Oct. 25, 1982), Abstract 141206M, p. 346.

Pacific North-West, Chemical Abstracts vol. 102, No. 23, (Jun. 10, 1985), Abstract 199459J, p. 212.

Chew et al., Chemical Extracts vol. 104, No. 7, (Feb. 17, 1986), Abstract 48583K, p. 310.

Wittwer et al., Chemical Abstracts vol. 106, No. 9 (Mar. 2, 1987), Abstract 64883E, p. 397.

*Primary Examiner*—Sam Rosen
*Attorney, Agent, or Firm*—Limbach, Limbach & Sutton

[57] ABSTRACT

Method for diluting blood, blood diluent, and antimicrobial agents and reagents, especially suitable for use in enumeration and sizing of blood cells. The antimicrobial agent in the blood diluent is potent, but relatively non-toxic to humans, and inexpensive. Furthermore, it does not interfere with blood analysis performed on an automated, blood-analysis instrument.

6 Claims, 2 Drawing Sheets

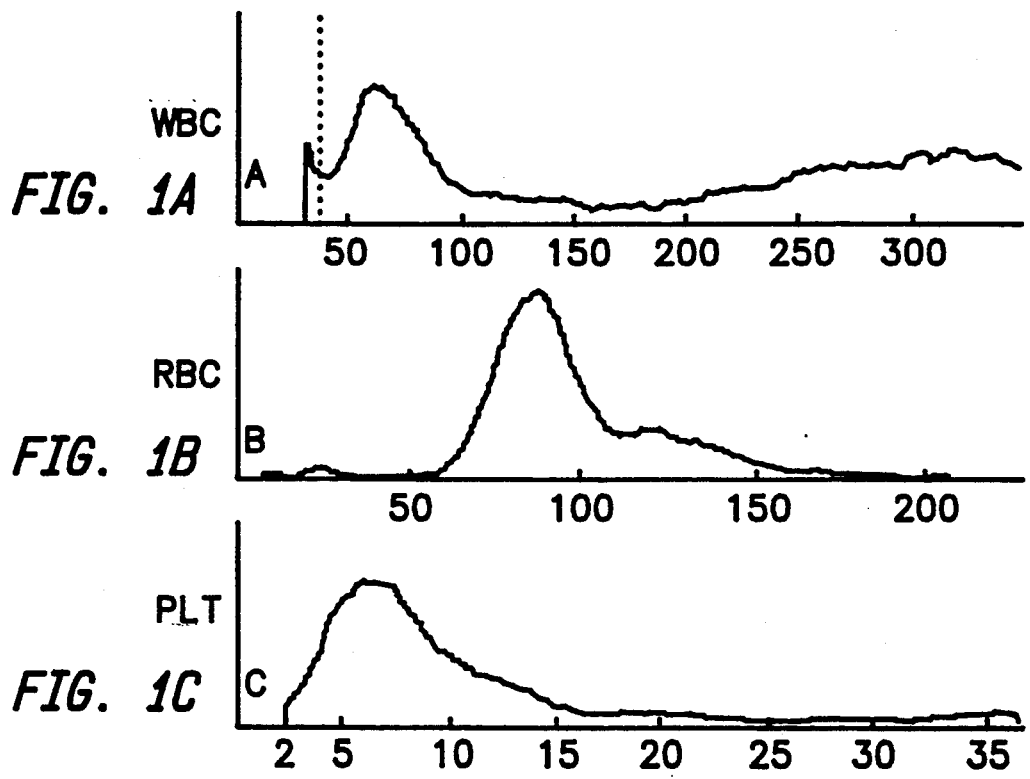
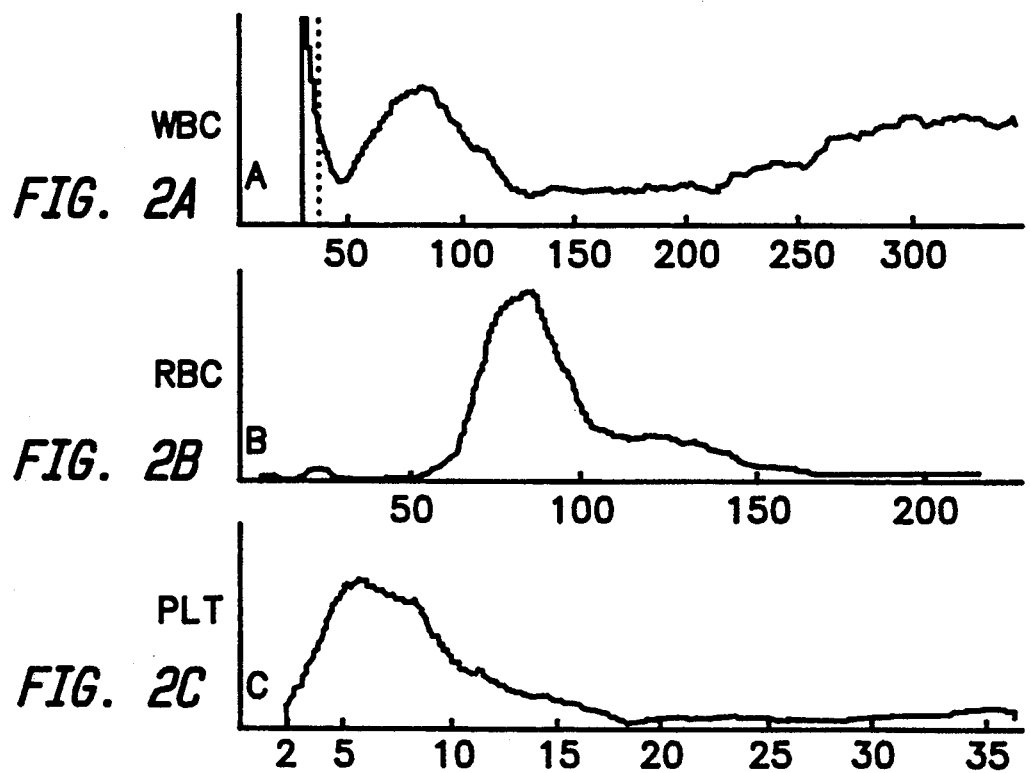

BLOOD DILUENT FOR RED BLOOD CELL ANALYSIS

BACKGROUND OF THE INVENTION

1. Field of the Invention

This invention concerns a method for diluting blood, blood diluent, and antimicrobial agents and reagents, especially suitable for use in enumeration and sizing of blood cells, including white blood cell subpopulations.

2. Description of the Prior Art

Analytical data of blood are important as an index of health and well being. The analysis of blood cell populations provides useful information for diagnosis and treatment, since they show a rapid response to variations in medical condition.

Most analytical methods rely on the fundamental cell property of volume regulation. Each type of cell in the circulating blood has its own characteristic volume, ranging from as small as 2 cubic microns for platelets to over 450 cubic microns for polymorphonuclear cells. Automated, blood-analysis instruments have been developed to accomplish the measurement of blood cells and related components with simplicity and rapidity. Such measurements include white blood cell count (WBC), red blood cell count (RBC), platelet count (PLT), hematocrit (HCT), hemoglobin (HGB), the mean corpuscular volume (MCV), the mean corpuscular hemoglobin (MCH), and the mean corpuscular hemoglobin concentration (MCHC), as well as WBC subpopulations such as lymphocytes, monocytes, and granulocytes.

Before making blood cells counts by means of an automated, blood-analysis instrument, the blood is diluted to a certain concentration. The diluent comprises a stable water solution of chemical salts providing an electrolytic solution capable of conducting current to which a blood sample can be added so as to dilute the red blood cells, white blood cells, platelets and other blood components and enable the desired parameters of these blood components to be measured, counted and evaluated. See, for example, U.S. Pat. Nos. 4,213,876, 4,244,837, 4,521,518 and 4,745,071.

In analyzing blood by an automated, blood-analysis instrument or other analytical method (including manual microscopic evaluations), it is essential that the diluent not adversely affect the chemical and physical integrity of the blood cells during the analysis. For instance, if the blood diluent is not isotonic and osmotically balanced with respect to the blood, the blood cells may shrink or expand. Importantly, The diluent should not adversely affect the blood analysis itself.

The diluent must also be free from particles which may interfere with the analysis of the blood. While the diluent is normally filtered to remove particles larger than 0.2 micron in diameter at the time of its manufacture, the diluent may be susceptible to the support of microorganism growth after the manufacture and packaging of the diluent. The presence of microorganisms may result in inaccurate and non-reproducible results.

It is a common practice to include a antimicrobial agent in blood diluents to retard the growth of microorganisms. The antimicrobial agent, as with other components of the diluent, must not adversely affect the blood cells or adversely affect or interfere with the analyses. Thus, while antimicrobial agents in blood diluents are desireable, caution must be observed in their selection and use.

An antimicrobial agent which has been employed for many years in blood diluents is sodium azide. Its use has not, however, been without significant problems. First, the presence of sodium azide has been found to influence the formation of cyanmethemoglobin, a chromogen formed for determining hemoglobin in a blood sample. For instance, without sodium azide in the diluent, the hemoglobin as determined photometrically may be significantly different than that with the azide present. Second, aqueous solutions of sodium azide are highly toxic (toxicity level of 6 on a scale of 1 to 6). See Gosselin et al. (eds.), Clinical Toxicology of Commercial Products, The Williams and Wilkins Company, Baltimore, 5th Edition, 1984, (Section IID, position 111). Finally, the disposal of sodium azide through copper or lead-containing plumbing systems may result in the formation of heavy metal azides and their buildup over extended period of time.

Despite the need for alternatives to sodium azide as an antimicrobial agent in blood diluents, few alternatives have been proposed. An attempt has been made to substitute other preservatives for sodium azide and an example of this is shown in U.S. Pat. Nos. 3,962,125 and 4,102,810 where 2-phenoxyethanol is used as an antimicrobial agent.

There are disadvantages to the use of phenoxyethanol as well. First, phenoxyethanol is a rather weak antimicrobial agent. It has been found to be more effective when used in conjunction with other preservatives, such as the hydroxybenzoates. Martindale, The Extra Pharmacopoeia (27th edition, The Pharmaceutical Press, London, 1977, page 1281). Second, while less toxic than sodium azide, phenoxyethanol is still toxic (toxicity level of 4 on a scale of 1 to 6). See Gosselin et al., supra (Section IID, position 463). Finally, in U.S. Pat. Nos. 3,962,125 and 4,102,810, sodium fluoride is essentially included along with phenoxyethanol in the proposed diluent to enhance hemoglobin chromogen formation. Sodium fluoride is only slightly less toxic than sodium azide (toxicity level of 4–5). See Gosselin et al., supra (Section IID, position 100).

A further attempt to substitute other preservatives for sodium azide can be found in U.S. Pat. No. 4,248,634, in which sodium dehydroacetate is used as an antimicrobial agent. Sodium dehydroacetate, a fungicide, is toxic at high doses but is less toxic than sodium azide, sodium fluoride, and phenoxyethanol (toxicity level of 3). See Gosselin et al., supra (Section IID, position 1187).

One object of the present invention is to provide an antimicrobial agent for a blood diluent that does not interfere with the blood analysis.

Another object of the present invention is to provide an antimicrobial agent for a blood diluent that is potent but relatively non-toxic.

Still another object of the present invention is to provide an antimicrobial agent that is potent but inexpensive.

Objects and advantages other than those above set forth will be apparent from the following description when read in connection with the accompanying drawings.

SUMMARY OF THE INVENTION

The invention is directed to a method for diluting blood, a blood diluent, and antimicrobial agent or reagent for use in a blood diluent. In a method of determining the number and size of cells in the blood wherein blood is diluted in an osmotically balanced solution, the improvement comprises employing EDTA alone, or EDTA and sodium fluoride together, as an antimicrobial reagent.

The blood diluent of the invention generally comprises an organic buffer adjusted to an appropriate pH, a cell stabilizing agent, an inorganic salt to adjust conductivity, ionic strength and osmolality, a solvent and EDTA, wherein EDTA serves as an antimicrobial agent, or a mixture of EDTA and sodium fluoride wherein together they serve as an antimicrobial reagent.

DESCRIPTION OF THE DRAWINGS

FIG. 1A, 1B and 1C are histograms showing the number of cells versus cell volume analyzed on an automated blood-analysis system using a standard diluent without any antimicrobial agents;

FIG. 2A, 2B and 2C are histograms showing the number of cells versus cell volume analyzed on an automated blood-analysis system using a standard diluent containing only sodium fluoride as an antimicrobial agent;

DESCRIPTION OF THE INVENTION

Figure 3A:
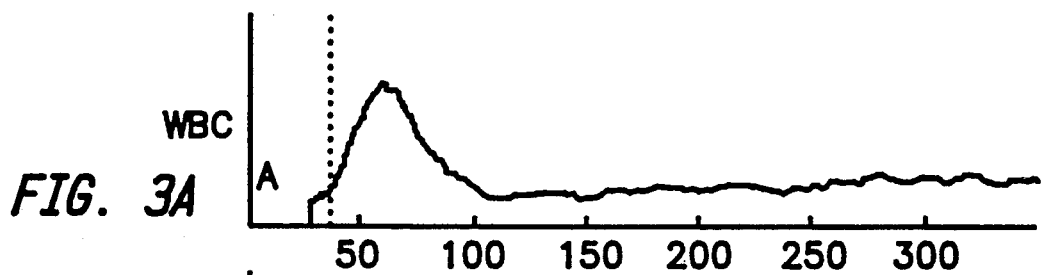
FIGS. 3A, 3B and 3C, are histograms showing the number of cells versus cell volume analyzed on an automated blood-analysis system using an embodiment of the present invention.

The present invention is directed to an antimicrobial agent for use in a diluent for analyzing population and subpopulation differentiation of blood cells in a sample of blood. Routinely, such analysis can be performed on an automated, blood-analysis instrument, such as, e.g., a Sequoia-Turner CELL-DYN® 2000 blood-analysis instrument, used in accordance with the instructions provided by the manufacturer. Of course, the properties of the present diluent make it multi-purpose, i.e. useful for other analytical methods for cells (including manual microscopic evaluations).

As noted above, it is a common practice to include a antimicrobial agent in blood diluents to retard the growth of microorganisms. The diluent used as a control in the experiments described below (hereinafter "the control diluent") uses 1-hydroxypyridine-2-thione as an antimicrobial agent and has the composition set forth in Table 1 of U.S. Pat. No. 4,745,071, which is hereby incorporated by reference. The control diluent has been used extensively and successfully for the analysis of blood cell populations on an automated, blood-analysis instrument, such as, e.g., a Sequoia-Turner CELL-DYN® 2000 blood-analysis instrument. Nonetheless, in the course of using the control diluent, some microbial growth was observed.

Preliminary visual analysis of the microbial growth in the control diluent suggested that it was not bacterial growth but was, rather, fungal growth. The presence of fungal growth and the absence of bacterial growth indicated that the antimicrobial agent of the control diluent, 1-hydroxypyridine-2-thione, is an effective bacteriostatic or bacteriocidal agent but not a fungistatic or fungicidal agent.

The present invention prevents microbial growth and, in particular, fungal growth, in a blood diluent. The diluent of the invention comprises an aqueous solution of a cell stabilizing agent, a bacteriostatic agent, an organic buffer adjusted to an appropriate pH, a fungistatic agent or reagent(s), and additional ionic components to provide a suitable ionic strength, and osmolality to maintain the normal volume of the cells.

The present diluent is a solution which includes various components well known in the art of blood cell analysis. For example, water is routinely used as the solvent, as it is inexpensive, safe and generally compatible with the sample to be analyzed.

The presently preferred cell stabilizing agent is 1,3-dimethylurea and the presently preferred organic buffer is N-(2-acetamido)-2-iminodiacetic acid (ADA). While these are the preferred compounds, the invention contemplates that other compounds, either presently known or equivalent compounds hereafter developed, might be substituted in their place. The pH of the buffered diluent is conveniently adjusted to approximately 6.9 with, e.g., sodium hydroxide, but other bases may be substituted and the pH may vary between at least 6.5 and 7.5 without substantially interfering with the proposed use of the diluent.

In addition, sodium chloride is routinely used to adjust the osmolality of the diluent to approximately 320 milliosmoles, which is known to be appropriate for maintaining normal blood cell volume. Obviously, other salts and other osmolality levels are possible. Sodium sulfate is generally used to give the diluent an appropriate ionic strength. However, other compounds with this property can be substituted.

The fungistatic agents or reagents of the present invention are (1) ethylenediaminetetraacetic acid (EDTA) alone or 2) EDTA in combination with sodium fluoride. The presently preferred composition of the diluent employing the former is illustrated in Table 1, while the preferred composition of the diluent containing the mixture of agents is illustrated in Table 2.

TABLE 1

| Diluent Compositions | | |
|---|---|---|
| Component | Range | Preferred |
| sodium sulfate | 8–12 grams | 10.0 grams |
| sodium chloride | 3–6 grams | 4.2 grams |
| 1,3 dimethylurea | 0.5–3.0 grams | 1.0 grams |
| 1-hydroxypyridine-2-thione | 0.05–2.0 grams | 0.1 grams |
| EDTA | 0.01–1.0 grams | 0.3 grams |
| ADA Buffer | 0.5–4.0 grams | 1.4 grams |
| sodium hydroxide | to obtain pH - 6.9 | 0.5 grams |
| water | sufficient to make one liter | |

TABLE 2

| Diluent Compositions | | |
|---|---|---|
| Component | Range | Preferred |
| sodium sulfate | 8–12 grams | 10.0 grams |
| sodium chloride | 3–6 grams | 4.2 grams |
| 1,3 dimethylurea | 0.5–3.0 grams | 1.0 grams |
| 1-hydroxypyridine-2-thione | 0.05–2.0 grams | 0.1 grams |
| EDTA | 0.01–1.0 grams | 0.3 grams |
| Sodium fluoride | 0.01–0.5 grams | 0.3 grams |
| ADA Buffer | 0.5–4.0 grams | 1.4 grams |
| sodium hydroxide | to obtain pH - 6.9 | 0.5 grams |
| water | sufficient to make one liter | |

Sodium fluoride is known as an excellent preservative of blood (Med J. Aust. 1:1939, 1968). Sodium fluoride is classified as a toxic substance (toxicity level 4–5 on a maximum scale of 6). See Gosselin et al., supra (Section IID, position 100).

By contrast, EDTA is not known for any antimicrobial properties. EDTA is relatively non-toxic; this acid and many of its salts bind metal cations tightly and so render then essentially innocuous. See Gosselin et al., supra (Section IID, position 1506). The calcium salt of EDTA is used intravenously to detoxify and enhance the renal excretion of lead. The calcium derivative (chelate) has a low toxicity in experimental animals (toxicity of 2 on a scale of 6) and the disodium salt can be tolerated at doses as higher than 1 gm/kg in mice (toxicity of approximately 3).

Experimental

In order to further describe the present invention, the following experiments were carried out to demonstrate the efficacy of EDTA and EDTA with sodium fluoride as antimicrobial agents by their impact on (1) automated, blood-analysis results and (2) microbial growth in culture.

All quantities labelled percent (%) are grams per 100 milliliters, unless otherwise indicated. All weights are given in grams (g) or milligrams (mg), all concentrations are given as millimolar (mM) or micromolar ($\mu$M) and all volumes are given in liters (L) or milliliters (ml) unless otherwise indicated.

EXAMPLE 1

Blood Analysis

Routine analysis of the white blood cell (WBC), red blood cell (RBC) and platelet (PLT) populations, as well as analysis of WBC subpopulations, of blood samples was performed on an automated, blood-analysis instrument (CELL-DYN ® 2000 blood-analysis instrument, Sequoia-Turner Corp., Mountain View, California), used in accordance with the instructions provided by the manufacturer.

FIGS. 1-4 show the impact of the antimicrobial agents of the present diluent on the analysis of population and subpopulation differentiation of blood cells. Because the cell volume of RBCs and WBCs overlap considerably, it is not possible to count one in the presence of the other by size discrimination alone. Thus, the diluent of the present invention must also serve as a diluent for a lytic reagent. A standard lytic reagent and method, such as that described in U.S. Pat. No. 4,745,071 is used to analyze each population separately and is hereby incorporated by reference.

Following the lysis step to separate WBCs from RBCs, WBC subpopulations can be examined. WBC subpopulation characterization is known in the art. See e.g., U.S. Pat. No. 4,485,175. Again, cells are differentiated on the basis of cell size. In this manner, three subpopulations can, in most instances, be identified. These three subpopulations are (in order of increasing size) lymphocytes, monocytes, and granulocytes. Granulocytes are a heterogeneous group that include neutrophils, eosinophils and basophils.

Blood cell population and subpopulation characterization is most useful in identifying pathological conditions. Pathological conditions may give rise to at least three types of variations in blood cell profile. First, the size of existing populations and/or subpopulations may be altered (e.g. larger WBCs). Second, the number of normal sized cells of an existing population or subpopulation may be altered (e.g. more monocytes). Finally, a completely different population or subpopulation may emerge (e.g. appearance of promyelocytes).

FIG. 1A shows the WBC histogram achieved on the instrument using the preferred diluent of Table 1, except that EDTA was not included. Three WBC subpopulations can be identified. The lymphocyte subpopulation peak (10) shows a mean cell volume of approximately 62 cubic microns. The monocyte subpopulation (11) ranges in size between approximately 80 and 180 cubic microns. The granulocyte subpopulation peak (12) shows a mean cell volume of approximately 320 cubic microns. Note that there is a relatively low level of cell stroma (13).

FIG. 1B shows the RBC histogram using the same diluent as in FIG. 1A. The mean cell volume for the RBC population peak (14) is approximately 86 microns. The histogram shows only this one peak which rises sharply and drops softly.

FIG. 1C shows the PLT histogram using the same diluent as in FIGS. 1A and 1B. The mean cell volume for the PLT population peak (15) is approximately 7 cubic microns.

FIGS. 2A-2C show the results of an experiment designed to assess the impact on the analysis of sodium fluoride alone. The diluent is the preferred diluent of Table 2, except that EDTA was not included. It was hoped that sodium fluoride could be used to prevent microbial growth. Unexpectedly, the addition of sodium fluoride causes the lymphocyte subpopulation peak (20) to shift to the right relative to the (control diluent) WBC population peak (10) of FIG. 1A; the mean cell volume is approximately 85 cubic microns. In this manner, the lymphocyte subpopulation peak (20) intrudes into the monocyte subpopulation range (21). Furthermore, the level of stroma (23) is dramatically and unacceptably increased. From FIG. 2B it appears that the RBC population peak (24) position is unchanged. However, from FIG. 2C, a distinct shift of the platelet population peak (25) to the left is observed.

From the results shown in FIGS. 2A-2C it is clear that when used alone, sodium fluoride interferes with the analysis by causing overlap between WBC subpopulations. As noted above, the identification of pathological conditions depends on the ability to detect variations in normal blood cell parameters. Overlap between WBC subpopulations would prevent such an identification.

Clearly, sodium fluoride, when used alone, is not a solution to the microbial growth problem. Nonetheless, further experiments revealed that sodium fluoride, when used in a diluent of a particular composition, could be used to prevent microbial growth. Surprisingly, while studying sodium fluoride in other diluents, it was discovered that the interference by sodium fluoride could be eliminated.

Figure 3B:
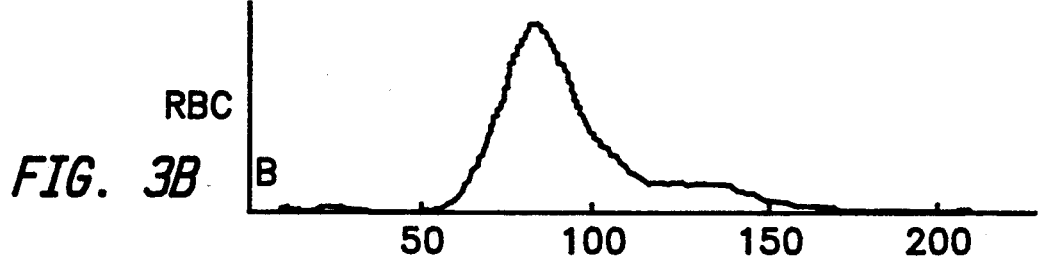
Figure 3C:
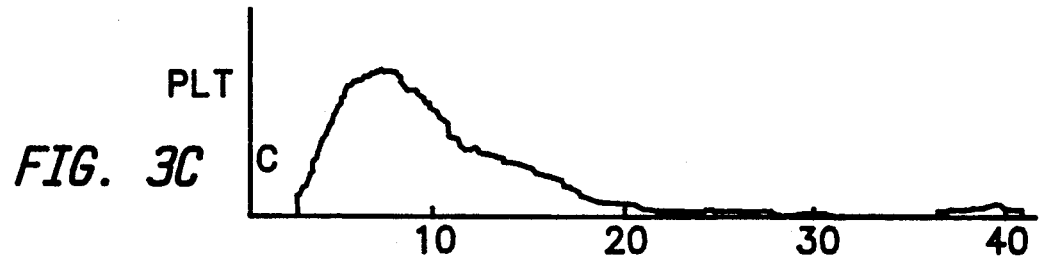

FIGS. 3A-3C show the results of an experiment where sodium fluoride is used in the presence of EDTA. The diluent is the preferred diluent of Table 2. FIG. 3A shows that, in the presence of EDTA, the addition of sodium fluoride does not cause the lymphocyte subpopulation peak (30) to intrude into the monocyte subpopulation range (31); the mean cell volume for the lymphocyte peak (30) is approximately 61 cubic microns. There is a very low level of cell stroma (33). FIGS. 3B (RBC population peak (34)) and 3C (platelet peak (35)) are similarly unchanged.

This surprising result prompted further experiments where the concentration of EDTA was held constant (0.3 gm/L) and a range (0.gm/L–0.5 gm/L) of sodium fluoride concentrations were assessed in separate diluents otherwise identical to the Table 2 preferred diluent. No interference with the analysis was observed.

Figure 4A:
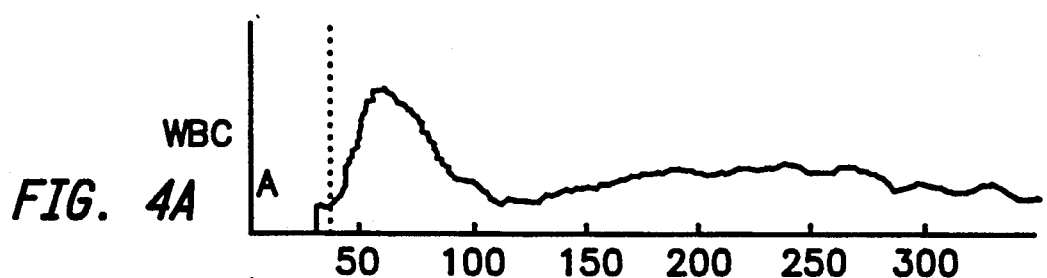
FIGS. 4A, 4B and 4C, are histograms showing the number of cells versus cell volume analyzed on an automated blood-analysis system using an alternative embodiment of the present invention.
Figure 4B:
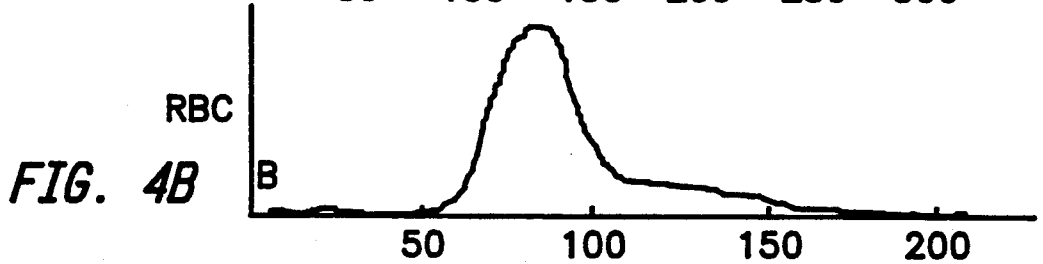
Figure 4C:
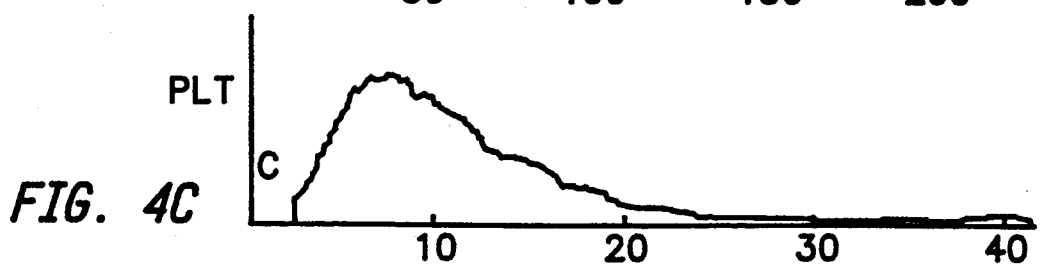

The impact, if any, of EDTA used alone is evaluated in FIGS. 4A–4C. The diluent was the preferred diluent of Table 1. FIG. 4A shows the lymphocyte subpopulation peak (40) to be unchanged relative to the comparable peak (10) of FIG. 1A; the mean cell volume is approximately 60 cubic microns Again, FIGS. 4B (RBC population peak (44)) and 4C (platelet peak (45)) are unchanged.

EXAMPLE 2

Microbial Growth

Microbial growth was assessed in culture experiments performed at Laboratory Services, Inc., San Jose, California. Samples were taken from diluents identical to that of Table 2 except for the concentrations of EDTA and sodium fluoride. Cultures were inoculated and incubated for fungus growth on Sabouraud Dextrose and Mycosel slants according to McGimis, *Laboratory Handbook of Medical Mycology*, Academic Press, 1980, pp. 74–77. This method was, thus, a "direct culture."

Samples were also used to inoculate thioglycollate broth. If growth was observed in the thioglycollate, samples from the broth were then used to inoculate Sabouraud Dextrose and Mycosel slants as a "subculture."

If growth appeared to be a yeast, standard methods were used to proceed with yeast identification. If growth appeared to be a fungus, the growing colony morphology was observed, a Lactophenol Cotton Blue prep was carried out according to *Laboratory Methods in Medical Mycology*, U.S. Dept. of HEW, Public Health Service, CDC, June 1978, pp. 29–30 and a slide culture was performed. The slide culture involved gently removing and mounting the coverslip of the Lactophenol Cotton Blue prep to observe the fruiting bodies of the fungus. Under a hood, two square plugs from a cornmeal agar plate are placed on the surface of the same plate with a sterile wooden stick. A small portion of unknown fungus colony, again with a sterile wooden stick, is then placed inside of the square "holes" and the top edges of the square plugs. Glass coverslips are then placed on top of each of the two square inoculate plugs and the plate is incubated at 30° C. When sufficient growth is observed, the reverse side of the plate is examined so that the inside edges of the square "holes" might be observed for fruiting bodies.

The results from these microbial studies are shown in Table 3 (only the concentrations of EDTA and sodium fluoride are shown).

TABLE 3

| Diluent Composition | Mycology Culture (7 days) | |
|---|---|---|
| | Direct Culture (30° C.) | Subculture (30° C.) |
| 0.0 gm/L EDTA & 0.0 gm/L NaF | PAECILOMYCES | PAECILOMYCES |
| 0.3 gm/L EDTA & 0.0 gm/L NaF | NO GROWTH | PAECILOMYCES |
| 0.3 gm/L EDTA & 0.1 gm/L NaF | NO GROWTH | PAECILOMYCES |
| 0.3 gm/L EDTA & 0.2 gm/L NaF | NO GROWTH | PAECILOMYCES |
| 0.3 gm/L EDTA & 0.3 gm/L NaF | NO GROWTH | PAECILOMYCES |

TABLE 3-continued

| Diluent Composition | Mycology Culture (7 days) | |
|---|---|---|
| | Direct Culture (30° C.) | Subculture (30° C.) |
| 0.3 gm/L EDTA & 0.4 gm/L NaF | NO GROWTH | NO GROWTH |

From the data it is clear that, when the diluent is formulated with only 1-hydroxypyridine-2-thione (0.1 gm/L) as an antimicrobial agent, growth of microorganisms occur. In a 7 day culture at 30° C., the primary microorganism is Paecilomyces.

The most surprising result of Table 3 is that both (1) EDTA alone and (2) EDTA and sodium fluoride together are effective at stopping growth in the direct cultures. This is unexpected in view of the fact that no antimicrobial property of EDTA has been heretofore described.

The subculture technique appears from the data of Table 3 to measure a different level of growth. This is probably due to the lower concentration of the antimicrobial agents when the diluent is put into the thioglycollate (1 ml into 15 ml). Interestingly, the combination of EDTA and sodium fluoride is effective in stopping growth in the subcultures when used in higher concentrations.

EXAMPLE 3

Concentration Analysis

The results of Table 3 prompted the study of higher concentrations of EDTA and sodium fluoride on arresting growth. Effective concentrations of EDTA and sodium fluoride that did not adversely impact the blood analysis were found to be:

EDTA (above 0.02 gm/L up to 1.0 gm/L)
Sodium Fluoride (above 0.02 gm/L up to 0.5 gm/L)

Thus it can be seen that the present invention provides a novel and improved method for determining the cell number and size of cell populations and subpopulations in a blood sample wherein the blood is diluted in an osmotically balanced solution. The invention also provides a novel blood diluent containing an antimicrobial agent for a blood diluent that does not interfere with the blood analysis, is potent, but relatively non-toxic and inexpensive.

It should be understood that various alternatives to the methods and materials herein disclosed may be employed in practicing the present invention. It is intended that the following claims define the invention, and that the materials and methods within the scope of these claims and their equivalents be covered thereby.

We claim:

1. A blood diluent useful in analysis of red blood cell number, and the enumeration of white blood cell populations and sub-populations in a whole blood sample, said diluent comprising an aqueous solution of:
   (a) sodium sulfate;
   (b) sodium chloride;
   (c) 1, 3 dimethylurea;
   (d) 1-hydroxypyridine-2-thione;
   (e) EDTA;
   (f) ADA Buffer; and,
   (g) sodium hydroxide to obtain pH 6.9, wherein said diluent is an electrolyte capable of conducting current, stabilizing red blood cell volumes and having no adverse effect on white blood cells.

2. A blood diluent useful in analysis of red blood cell number, and the enumeration of white blood cell populations and sub-populations in a whole blood sample, said diluent comprising:
- (a) between 8.0 and 12.0 grams sodium sulfate,
- (b) between 3.0 and 6.0 grams sodium chloride;
- (c) between 0.5 and 3.0 grams 1,3 dimethylurea;
- (d) between 0.05 and 2.0 grams 1-hydroxypyridine-2-thione;
- (e) between 0.01 and 1.0 grams EDTA;
- (f) between 0.5 and 4.0 grams ADA Buffer;
- (g) sodium hydroxide to obtain pH 6.9; and
- (h) sufficient water to make one liter of diluent, wherein said diluent is an electrolyte capable of conducting current, stabilizing red blood cell volumes and having no adverse effect on white blood cells.

3. A blood diluent useful in analysis of red blood cell number, and the enumeration of white blood cell populations and sub-populations in a whole blood sample, said diluent comprising:
- (a) 10.0 grams sodium sulfate;
- (b) 4.2 grams sodium chloride;
- (c) 1.0 grams 1,3 dimethylurea;
- (e) 0.3 grams EDTA;
- (f) 1.4 grams ADA Buffer;
- (g) 0.5 grams sodium hydroxide to obtain pH 6.9; and
- (h) sufficient water to make one liter of diluent, wherein said diluent is an electrolyte capable of conducting current stabilizing red blood cell volumes and having no adverse effect on white blood cells.

4. A blood diluent useful in analysis of red blood cell number, and the enumeration of white blood cell populated and sub-populations in a whole blood sample, said diluent comprising an aqueous solution of:
- (a) sodium sulfate;
- (b) sodium chloride;
- (c) 1,3 dimethylurea;
- (d) 1-hydroxypyridine-2-thione;
- (e) EDTA;
- (f) sodium fluoride;
- (g) ADA Buffer; and,
- (h) sodium hydroxide to obtain pH 6.9, wherein said diluent is ;an electrolyte capable of conducting current, stabilizing red blood cell volumes and having no adverse effect on white blood cells.

5. A blood diluent useful in analysis of red blood cell number, and the enumeration of white blood cell populations and sub-populations in a whole blood sample, said diluent comprising:
- (a) between 8.0 and 12.0 grams sodium sulfate;
- (b) between 3.0 and 6.0 grams sodium chloride ;
- (c) between 0.5 and 3.0 grams, 1,3 dimethylurea;
- (d) between 0.5 and 2.0 grams 1-hydroxypyridine-2-thione;
- (e) between 0.01 and 1.0 grams EDTA;
- (f) between 0.01 and 0.5 grams sodium fluoride;
- (g) between 0.5 and 4.0 grams ADA Buffer;
- (h) sodium hydroxide to obtain pH 6.9; and
- (i) sufficient water to make one liter of diluent, wherein said diluent is an electrolyte capable of conducting current stabilizing red blood cell volumes and having no adverse effect on white blood cells.

6. A blood diluent useful in analysis of red blood cell number, and the enumeration of white blood cell populations and sub-populations in a whole blood sample, said diluent comprising:
- (a) 10.0 grams sodium sulfate;
- (b) 4.2 grams sodium chloride;
- (c) 1.0 grams 1,3 di-methylurea;
- (d) 0.1 grams 1-hydroxypyridine-2-thione;
- (e) 0.3 grams EDTA;
- (f) 0.3 grams sodium fluoride;
- (g) 1.4 grams ADA Buffer;
- (h) 0.5 grams sodium hydroxide to obtain pH 6.9; and
- (i) sufficient water to make one liter of diluent, wherein said diluent is an electrolyte capable of conducting current, stabilizing red blood cell volumes and having no adverse effect on white blood cells.

* * * * *